US008821837B2

(12) United States Patent
Perez et al.

(10) Patent No.: US 8,821,837 B2
(45) Date of Patent: Sep. 2, 2014

(54) AQUEOUS METHOD OF MAKING MAGNETIC IRON OXIDE NANOPARTICLES

(71) Applicant: University of Central Florida Research Foundation, Inc., Orlando, FL (US)

(72) Inventors: Jesus Manuel Perez, Orlando, FL (US); Sudip Nath, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/855,706

(22) Filed: Apr. 2, 2013

(65) Prior Publication Data

US 2013/0330280 A1 Dec. 12, 2013

Related U.S. Application Data

(63) Continuation of application No. 12/174,169, filed on Jul. 16, 2008, now Pat. No. 8,409,463.

(60) Provisional application No. 60/949,945, filed on Jul. 16, 2007.

(51) Int. Cl.
*A61B 5/055* (2006.01)
*A61K 49/18* (2006.01)
*C01G 49/08* (2006.01)

(52) U.S. Cl.
CPC ......... *A61K 49/1863* (2013.01); *C01P 2004/16* (2013.01); *C01P 2004/32* (2013.01); *C01P 2002/85* (2013.01); *C01P 2004/84* (2013.01); *C01P 2004/04* (2013.01); *C01P 2002/72* (2013.01); *C01P 2006/42* (2013.01); *C01G 49/08* (2013.01); *A61K 49/1848* (2013.01); *C01P 2004/62* (2013.01)
USPC ...................................... 424/9.322

(58) Field of Classification Search
CPC . C01G 49/08; C01P 2002/72; C01P 2002/85; C01P 2004/04; C01P 2004/16; C01P 2004/32; C01P 2004/62; C01P 2004/84; C01P 2006/42
USPC ...................................... 424/9.322
See application file for complete search history.

(56) References Cited

U.S. PATENT DOCUMENTS

| | | |
|---|---|---|
| 5,164,297 A | 11/1992 | Josephson |
| 5,254,460 A | 10/1993 | Josephson |
| 5,660,990 A | 8/1997 | Rao |
| 6,661,221 B2 | 12/2003 | Taguchi |
| 6,891,368 B2 | 5/2005 | Kawano |
| 7,531,149 B2 | 5/2009 | Peng |
| 8,409,463 B1 | 4/2013 | Perez |
| 2002/0151787 A1 | 10/2002 | Bjornerud |
| 2003/0092029 A1 | 5/2003 | Josephson |
| 2003/0124194 A1 | 7/2003 | Gaw |
| 2004/0086885 A1 | 5/2004 | Lee |
| 2006/0275757 A1 | 12/2006 | Lee |
| 2006/0286379 A1 | 12/2006 | Gao |
| 2007/0020701 A1 | 1/2007 | Menon |
| 2007/0090323 A1* | 4/2007 | Duguet et al. ............. 252/62.56 |
| 2010/0072994 A1 | 3/2010 | Lee |
| 2011/0021374 A1 | 1/2011 | Lee |

FOREIGN PATENT DOCUMENTS

| | | |
|---|---|---|
| EP | 1260595 | 11/2002 |
| EP | 0805343 | 7/2003 |
| EP | 1458031 | 1/2005 |
| EP | 1631318 | 11/2010 |
| EP | 2710151 | 3/2014 |
| WO | WO 03/072830 | 9/2003 |
| WO | WO 2004/003508 | 1/2004 |
| WO | WO 2009/085214 | 7/2009 |
| WO | WO 2012/159121 | 11/2012 |

OTHER PUBLICATIONS

Jiang et al ( "Preparation and properties of superparamagnetic nanoparticles with narrow size distribution and biocompatible," Journal of Magnetism and Magnetic Materials 283 (2004) 210-14)).*
Baghi M, et al. (2005) The efficacy of MRI with ultrasmall superparamagnetic iron oxide particles (USPIO) in head and neck cancers. Anticancer Res. 25: 3665-3670.
Corr SA, et al. (2008) From Nanocrystals to Nanorods: New Iron Oxide—Silica Nanocomposites from Metallorganic Precursors. 112: 1008-1018.
Culp JT, et al. (2003) Monolayer, bilayer, multilayers: evolving magnetic behavior in Langmuir-Blodgett films containing a two-dimensional iron-nickel cyanide square grid network. Inorg Chem. 42: 2842-2848.
Enpuka K. (2005) Magnetic immunoassay with SQUID and magnetic marker. Digests of the IEEE International. 413-415.
Fazzina D. (2007) 7347-Facile Synthesis of Highly Magnetic Polymer Coated Iron Oxide Particles for Sensing Applications. NERAC, Inc. Research Report No. 10032825 (Tolland, CT) (2 pages).
Fujii T, et al. (1999) In situ XPS analysis of various iron oxide films grown by NO2-assisted molecular-beam epitaxy. Phys Rev. 59: 3195-9202.
Gao LZJ, et al. (2007) Intrinsic peroxidase-like activity of ferromagnetic nanoparticles. Nat Nanotechnol. 2: 577-583.

(Continued)

*Primary Examiner* — Suzanne Ziska
(74) *Attorney, Agent, or Firm* — Ballard Spahr LLP

(57) ABSTRACT

The invention discloses an aqueous method of making polymer coated superparamagnetic nanoparticles. Nanoparticles made by the method are included in the invention.

12 Claims, 15 Drawing Sheets

(56) References Cited

OTHER PUBLICATIONS

Gass J, et al. (2006) Superparamagnetic Polymer Nanocomposites with Uniform Fe3O4 Nanoparticle Dispersions. Advanced Functional Materials. 16: 71-75.
Goya GFB, et al. (2003) Static and dynamic magnetic properties of spherical magnetite nanoparticles. J Appl Phys. 94: 3520.
Gupta AK, et al. (2004) Surface modified superparamagnetic nanoparticles for drug delivery: interaction studies with human fibroblasts in culture. J Mater Sci Mater Med. 15: 493-496.
Gupta AK, et al. (2005) Synthesis and surface engineering of iron oxide nanoparticles for biomedical applications. Biomaterials. 26: 3995-4021.
Hellstern D, et al. (2006) Systemic distribution and elimination of plain and with Cy3.5 functionalized poly(vinyl alcohol) coated superparamagnetic maghemite nanoparticles after intraarticular injection in sheep in vivo. J Nanosci Nanotechnol. 6: 3261-3268.
Hu J, et al. (2001) Linearly polarized emission from colloidal semiconductor quantum rods. Science. 292: 2060-2063.
Ito A, et al. (2004) Magnetite nanoparticle-loaded anti-HER2 immunoliposomes for combination of antibody therapy with hyperthermia. Cancer Lett. 212: 167-175.
Jaiswal JK, et al. (2004) Synaptotagmin VII restricts fusion pore expansion during lysosomal exocytosis. PLoS Biol. 2: E233.
Jiang W, et al. (2004) Preparation and properties of superparamagnetic nanoparticles with narrow size distribution and biocompatible. Journal of Magnetism and Magnetic Materials. 283-210-241.
Josephson L, et al. (1999) High-efficiency intracellular magnetic labeling with novel superparamagnetic-Tat peptide conjugates. Bioconjug Chem. 10: 186-191.
Jun Y, et al. (2005) Nanoscale size effect of magnetic nanocrystals and their utilization for cancer diagnosis via magnetic resonance imaging. J Am Chem Soc. 127: 5732-5733.
Kaittanis C, et al. (2007) One-step, nanoparticle-mediated bacterial detection with magnetic relaxation. Nano Lett. 7: 380-383.
Kaittanis C, et al. (2012) Rapid and sensitive detection of an intracellular pathogen in human peripheral leukocytes with hybridizing magnetic relaxation nanosensors. PLoS One. 7(4):e35326.
Kohler N, et al. (2005) Methotrexate-modified superparamagnetic nanoparticles and their intracellular uptake into human cancer cells. Langmuir. 21: 8858-8864.
Lee H, et al. (2006) Antibiofouling polymer-coated superparamagnetic iron oxide nanoparticles as potential magnetic resonance contrast agents for in vivo cancer imaging. J Am Chem Soc. 128: 7383-7389.
Li W, et al. (2006) Multiamino-functionalized carbon nanotubes and their applications in loading quantum dots and magnetic nanoparticles. J Mater Chem. 16: 1852-1859.
Magana D, et al. (2006) Switching-on superparamagnetism in Mn/CdSe quantum dots. J Am Chem Soc. 128: 2931-2939.
Manna LS, et al. (2000) Synthesis of Soluble and Processable Rod-, Arrow-, Teardrop-, and Tetrapod-Shaped CdSe Nanocrystals. J. Am. Chem. Soc. 122: 12700-12706.
Melosh NA, et al. (2003) Ultrahigh-density nanowire lattices and circuits. Science. 300: 112-115.
Nath S, et al. (2009) Synthesis, magnetic characterization and sensing applications of novel dextran-coated iron oxide nanorods. Chem Mater. 21(8): 1761-1767.
Nath S, et al. (2008) Dextran-coated gold nanoparticles for the assessment of antimicrobial susceptibility. Anal Chem. 80: 1033-1038.
Nedeljkovic D, et al. (2004) Application of Permanent Magnetic Powder for Magnetic Field Sensing Elements. Rom Journ Phys. 50: 971-976.
Park SJ, et al. (2000) Synthesis and Magnetic Studies of Uniform Iron Nanorods and Nanospheres. J Am Chem Soc. 122: 8581-8582.
Peng X, et al. (2000) Shape control of CdSe nanocrystals. Nature. 404: 59-61.

Perez JM, et al. (2002a) Magnetic relaxation switches capable of sensing molecular interactions. Nat Biotechnol. 20: 816-820.
Perez JM, et al. (2002b) DNA-based magnetic nanoparticle assembly acts as a magnetic relaxation nanoswitch allowing screening of DNA-cleaving agents. J Am Chem Soc. 124: 2856-2857.
Perez JM, et al. (2003) Viral-induced self-assembly of magnetic nanoparticles allows the detection of viral particles in biological media. J Am Chem Soc. 125: 10192-10193.
Perez JM, et al. (2004) Use of magnetic nanoparticles as nanosensors to probe for molecular interactions. Chembiochem. 5: 261-264.
Perez JM, et al. (2008) Synthesis of biocompatible dextran-coated nanoceria with pH-dependent antioxidant properties. Small. 4: 552-556.
Perez JM. (2007) Iron oxide nanoparticles: hidden talent. Nat Nanotechnol. 2: 535-536.
Puntes VF, et al. (2001) Colloidal nanocrystal shape and size control: the case of cobalt. Science. 291: 2115-2117.
Radojevic V, et al. (2004) Process of Coating Optical Fiber with Composite Coating: Composite Coating: Magnetic Powder-Polymer. Powder metallurgy; Euro PM2004. 533-538.
Shen T, et al. (1993) Monocrystalline iron oxide nanocompounds (MION): physicochemical properties. Magn Reson Med. 29: 599-604.
Thorek DL, et al. (2006) Superparamagnetic iron oxide nanoparticle probes for molecular imaging. Ann Biomed Eng. 34: 23-38.
Wang DH, et al. (2004) Superparamagnetic Fe2O3 Beads—CdSe/ZnS Quantum Dots Core—Shell Nanocomposite Particles for Cell Separation. Nano Lett. 4: 409-413.
Wang JP, et al. (2004) Growth of magnetite nanorods along its easy-magnetization axis of [1 1 0]. J Cryst Growth. 263: 616-619.
Zhao YM, et al. (2006) Growth and characterization of iron oxide nanorods/nanobelts prepared by a simple iron-water reaction. Small. 2: 422-427.
Zou G, et al. (2005) Fe3O4 nanocrystals with novel fractal. J Phys Chem B. 109: 18356-18360.
Non-Final Office Action issued Jun. 9, 2011 for U.S. Appl. No. 12/174,169 filed on Jul. 16, 2008 (Perez et al.—inventors) (11 pages).
Examiner Interview Summary issued Oct. 20, 2011 for U.S. Appl. No. 12/174,169 filed on Jul. 16, 2008 (Perez et al.—inventors) (3 pages).
Response to Non-Final Office Action filed Oct. 28, 2011 for U.S. Appl. No. 12/174,169 filed on Jul. 16, 2008 (Perez et al.—inventors) (12 pages).
Non-Final Office Action issued Jan. 3, 2012 for U.S. Appl. No. 12/174,169 filed on Jul. 16, 2008 (Perez et al.—inventors) (13 pages).
Examiner Interview Summary issued Mar. 6, 2012 for U.S. Appl. No. 12/174,169 filed on Jul. 16, 2008 (Perez et al.—inventors) (3 pages).
Informal or Non-Responsive Amendment filed Apr. 27, 2012 for U.S. Appl. No. 12/174,169 filed on Jul. 16, 2008 (Perez et al.—inventors) (10 pages).
Notice of Non-Compliant Amendment issued May 2, 2012 for U.S. Appl. No. 12/174,169 filed on Jul. 16, 2008 (Perez et al.—inventors) (1 page).
Response to Non-Final Office Action filed Jun. 4, 2012 for U.S. Appl. No. 12/174,169 filed on Jul. 16, 2008 (Perez et al.—inventors) (6 pages).
Final Office Action issued Aug. 10, 2012 for U.S. Appl. No. 12/174,169 filed on Jul. 16, 2008 (Perez et al.—inventors) (13 pages).
Response to Final Office Action filed Oct. 10, 2012 for U.S. Appl. No. 12/174,169 filed on Jul. 16, 2008 (Perez et al.—inventors) (7 pages).
Advisory Action issued Nov. 6, 2012 for U.S. Appl. No. 12/174,169 filed on Jul. 16, 2008 (Perez et al.—inventors) (3 pages).
Response to Final Office Action filed Nov. 9, 2012 for U.S. Appl. No. 12/174,169 filed on Jul. 16, 2008 (Perez et al.—inventors) (4 pages).
Amendment After Final issued Nov. 30, 2012 for U.S. Appl. No. 12/174,169 filed on Jul. 16, 2008 (Perez et al.—inventors) (1 page).
Notice of Allowance and Fee(s) Due issued Nov. 30, 2012 for U.S. Appl. No. 12/174,169 filed on Jul. 16, 2008 (Perez et al.—inventors) (5 pages).
Amendment After Notice of Allowance filed Jan. 18, 2013 for U.S. Appl. No. 12/174,169 filed on Jul. 16, 2008 (Perez et al.—inventors) (3 pages).

(56) References Cited

OTHER PUBLICATIONS

Response to Amendment under Rule 312 issued Feb. 4, 2013 for U.S. Appl. No. 12/174,169 filed on Jul. 16, 2008 (Perez et al.—inventors) (4 pages).
Issue Notification issued Mar. 13, 2013 for U.S. Appl. No. 12/174,169 filed on Jul. 16, 2008 (Perez et al.—inventors) (1 page).
Response to Final Office Action with Rule 1.132 Declaration filed Jan. 17, 2014 for U.S. Appl. No. 12/258,785 filed on Oct. 27, 2008 (Inventors—Perez et al.) (11 pages).
Notice of Panel Decision from Pre-Appeal Brief Review mailed Oct. 23, 2013 for U.S. Appl. No. 12/258,785 filed on Oct. 27, 2008 (Inventors—Perez et al.) (2 pages).
Notice of Panel Decision from Pre-Appeal Brief Review mailed Aug. 1, 2013 for U.S. Appl. No. 12/258,785 filed on Oct. 27, 2008 (Inventors—Perez et al.) (2 pages).
Pre-Appeal Brief Request for Review filed Jun. 20, 2013 for U.S. Appl. No. 12/258,785 filed on Oct. 27, 2008 (Inventors—Perez et al.) (6 pages).
Final Office Action mailed Mar. 20, 2013 for U.S. Appl. No. 12/258,785 filed on Oct. 27, 2008 (Inventors—Perez et al.) (13 pages).
Response to Non-Final Office Action filed Nov. 28, 2012 for U.S. Appl. No. 12/258,785 filed on Oct. 27, 2008 (Inventors—Perez et al.) (14 pages).
Non-Final Office Action mailed Sep. 28, 2012 for U.S. Appl. No. 12/258,785 filed on Oct. 27, 2008 (Inventors—Perez et al.) (21 pages).
Notice of Panel Decision from Pre-Appeal Brief Review mailed Aug. 3, 2012 for U.S. Appl. No. 12/258,785 filed on Oct. 27, 2008 (Inventors—Perez et al.) (2 pages).
Pre-Appeal Brief Request for Review filed Jun. 27, 2012 for U.S. Appl. No. 12/258,785 filed on Oct. 27, 2008 (Inventors—Perez et al.) (4 pages).
Final Office Action mailed Feb. 27, 2012 for U.S. Appl. No. 12/258,785 filed on Oct. 27, 2008 (Inventors—Perez et al.) (9 pages).
Response to Notice of Non-Compliant Amendment filed Sep. 28, 2011 for U.S. Appl. No. 12/258,785 filed on Oct. 27, 2008 (Inventors—Perez et al.) (5 pages).
Notice of Non-Compliant Amendment mailed Sep. 6, 2011 for U.S. Appl. No. 12/258,785 filed on Oct. 27, 2008 (Inventors—Perez et al.) (2 pages).
Response to Non-Final Office Action filed Aug. 29, 2011 for U.S. Appl. No. 12/258,785 filed on Oct. 27, 2008 (Inventors—Perez et al.) (11 pages).
Non-Final Office Action mailed Apr. 28, 2011 for U.S. Appl. No. 12/258,785 filed on Oct. 27, 2008 (Inventors—Perez et al.) (6 pages).
Response to Notice of Non-Compliant Amendment filed Feb. 18, 2011 for U.S. Appl. No. 12/258,785 filed on Oct. 27, 2008 (Inventors—Perez et al.) (5 pages).
Notice of Non-Compliant Amendment mailed 01/24/100 for U.S. Appl. No. 12/258,785 filed on Oct. 27, 2008 (Inventors—Perez et al.) (2 pages).
Response to Restriction Requirement filed Jan. 20, 2011 for U.S. Appl. No. 12/258,785 filed on Oct. 27, 2008 (Inventors—Perez et al.) (6 pages).
Restriction Requirement mailed Dec. 20, 2012 for U.S. Appl. No. 12/258,785 filed on Oct. 27, 2008 (Inventors—Perez et al.) (5 pages).
International Preliminary Report on Patentability issued Nov. 28, 2013 for PCT Application No. PCT/US2012/038903 filed May 21, 2012 and published as WO 2012/159121 on 11/122/2012 (Inventors—Perez et al. // Applicant—University of Central Florida Research Foundation) (5 pages).
International Search Report issued Jan. 28, 2013 and published as WO 2012/159121 on 11/122/2012 (Inventors—Perez et al. // Applicant—University of Central Florida Research Foundation) (4 pages).
Written Opinion issued Jan. 28, 2013 and published as WO 2012/159121 on 11/122/2012 (Inventors—Perez et al. // Applicant—University of Central Florida Research Foundation) (4 pages).
Response to Notification of Missing Requirements filed Apr. 14, 2014 for U.S. Appl. No. 14/118,834 filed Nov. 19, 2013 (Inventors—Saleh Naser, et al.) (4 pages).
Preliminary Amendment filed Nov. 19, 2013 for U.S. Appl. No. 14/118,834 filed Nov. 19, 2013 (Inventors—Saleh Naser, et al.) (4 pages).

* cited by examiner (a)

(b)

AQUEOUS METHOD OF MAKING MAGNETIC IRON OXIDE NANOPARTICLES

CROSS-REFERENCE TO RELATED APPLICATIONS

This is a continuation of application Ser. No. 12/174,169 filed on Jul. 16, 2008 and titled "Aqueous Method for Making Magnetic Iron Oxide Nanoparticles," which claims priority from provisional application No. 60/949,945 filed on Jul. 16 2007. Both of these applications are incorporated herein by reference in their entireties.

STATEMENT REGARDING FEDERALLY SPONSORED RESEARCH OR DEVELOPMENT

This invention was made with government support under National Institutes of Health grant number K01CA101781. The government has certain rights in the invention.

FIELD OF THE INVENTION

The present invention relates to the field of biosensors and, more particularly to a method of making magnetic iron oxide nanoparticles coated with a polymer and functionalized with a ligand and the nanoparticles made accordingly.

BACKGROUND OF THE INVENTION

Iron oxide based magnetic nanocrystals have been widely used in a variety of biomedical applications such as diagnostic, magnetic resonance imaging (MRI) and in magnetically guided site specific drug delivery systems. Their use as MRI contrast agents and as an enhancer in hypothermia (heating of diseased tissue by application of an RF pulse) has been widely discussed in the literature. Recently, it has been found that dextran coated iron oxide nanoparticles, ranging in size from 1 to 100 nm, can be used as magnetic relaxation switches (MRS) or magnetic relaxation nanosensors (MRnS). When these nanosensors self assemble in the presence of a molecular target, there is a significant change in the spin spin relaxation time (T2) of neighboring water molecules. This parameter (T2) is a component of the MR signal. The observed target-induced self assembly of iron oxide based nanoparticles has been used as a sensitive detection method for various targets and reported in the literature.

SUMMARY OF THE INVENTION

With the foregoing in mind, the present invention advantageously provides iron oxide nanoparticles that have been specifically prepared for in vivo studies and for clinical applications, as injectable MRI contrast agents.

Monodisperse, water-soluble dextran-coated iron oxide nanorods were synthesized using a facile and scalable method. Our room temperature method involves the mixing of an acidic solution of iron salts with a basic solution of ammonium hydroxide to facilitate initial formation of iron oxide crystals. The stability, cystallinity and shape of these nanorods depend on the time of addition of the dextran as well its degree of purity. The as-synthesized nanorods exhibit unique magnetic properties, including superparamagnetic behavior and high spin-spin water relaxivity (R2). Additionally, they posses enhanced peroxidase activity when compared to those reported in the literature for spherical iron oxide nanoparticles. Thus, this high yield synthetic method for polymer-coated iron oxide nanorod will expedite their use in applications from magnetic sensors, devices and nanocomposites with magnetic and catalytic properties.

Iron oxide based magnetic nanoparticles have been widely used in a variety of biomedical applications such as magnetic separation, magnetic resonance imaging, hyperthermia, magnetically-guided drug delivery, tissue repair, and molecular diagnostics. For most applications, a polymeric coating is needed to improve the nanoparticles' aqueous stability, biocompatibility and conjugation properties. Typically, dextran-coated iron oxide nanoparticles have been successfully used as magnetic resonance imaging (MRI) contrast agent, due to their strong ability to dephase water protons in surrounding tissue, which results in a decrease in the MRI signal. In addition, the dextran coating can be crosslinked and functionalized with amino groups to facilitate the conjugation of targeting ligands for MRI and in vitro diagnostics applications. Current synthetic procedures for dextran-coated iron oxide nanoparticles involve the formation of the iron oxide core in the presence of dextran, as stabilizer and capping agent, in an alkaline solution. Under these in situ conditions, the nature, quality and amount of the polymer modulate the nucleation, growth and size of the newly formed iron oxide nanocrystal. A common characteristic of most reported in situ dextran-coated iron oxide nanoparticles synthetic procedures is the formation of nanoparticles with a spherical iron oxide core. Research efforts have been geared towards the production of small, uniform and highly dispersed spherical nanocrystals. Only recently, has the importance of the nanoparticles' shape been recognized, in particular one dimensional (1-D) structures such as nanorods and nanotubes, because they exhibit unique properties that are different from their corresponding zero dimensional counterparts (0-D or spherical nanocrystals). Particularly in the case of iron oxide, 1-D nanorods have been found to exhibit interesting magnetic properties due to their shape anisotropy, such as higher blocking temperatures and larger magnetization coercivity, compared to their 0-D counterparts. However, their wide application in biomedical research has been hampered by difficult and non-reproducible synthetic procedures, use of toxic reagents and poor yields. For instance, current methods for making iron oxide nanorods involve hydrothermal, sol-gel and high temperature procedures, among others. Therefore, a water-based synthetic procedure for iron oxide nanorods that is simple, economical, low temperature and high yield would be in high demand. In particular, synthetic methods that yield water soluble and stable polymer-coated nanorods would be ideal for studies geared towards the development of magnetic biosensors and magnetic devices.

For these reasons, we surmised it would also be advantageous to develop a new, facile, reproducible and low cost method to synthesize iron oxide nanoparticles for in vitro applications. In particular, a simple synthetic method that yields larger nanoparticles (100-500 nm) with a unique crystal shape and enhanced magnetic relaxation (high R2 and R1) would be helpful in studying the effect of shape and size on the sensitivity of the MRS assay.

To our understanding, it has not yet been reported what effect larger nanoparticles (100 to 500 nm) would have on the sensitivity of the magnetic relaxation assay. It has always been hypothesized that the target induced self assembly of large nanoparticles would result in nanoparticles clusters too big that they would settle down (precipitate) and therefore would render the system useless. However, if these nanoparticles contain a large iron oxide crystal with a high magnetic relaxation (high R2), a lower amount of nanoparticles would be required to achieve a detectable T2 signal (MRI signal). In such case. the amount of nanoparticles that participate in cluster formation would be small, resulting in smaller clusters of magnetic nanoparticles that remain suspended in solution and do not precipitate out. We hypothesized that having a lower number of nanoparticles participating in target-induced cluster formation would result in a more sensitive assay, having a lower detection limit.

Accordingly, here we disclose a facile, high-yield, room-temperature, and water-based synthetic protocol that yields disperse dextran-coated iron oxide nanorods (DIONrods). Our synthetic procedure differs from previously reported methods for dextran-coated iron oxide nanoparticles in that the dextran is not present during the initial nucleation process. Instead, the dextran is added at a later stage. This "stepwise" process, as opposed to the in situ process, allows for the formation of stable, disperse and highly crystalline superparamagnetic iron oxide nanorods with unique magnetic properties, such as high blocking temperature and improved high water relaxivity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1:
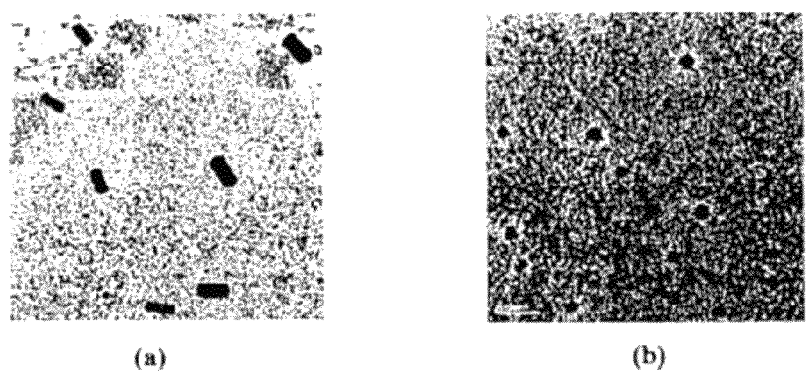
FIG. 1, according to an embodiment of the present invention, is a TEM image of aminated (a) dextran and (b) silica coated iron oxide nanoparticles; the TEM images show that the dextran coated nanoparticles are rod shaped whereas the silica ones are spherical in nature (Bar=500 nm)
Figure 7A:
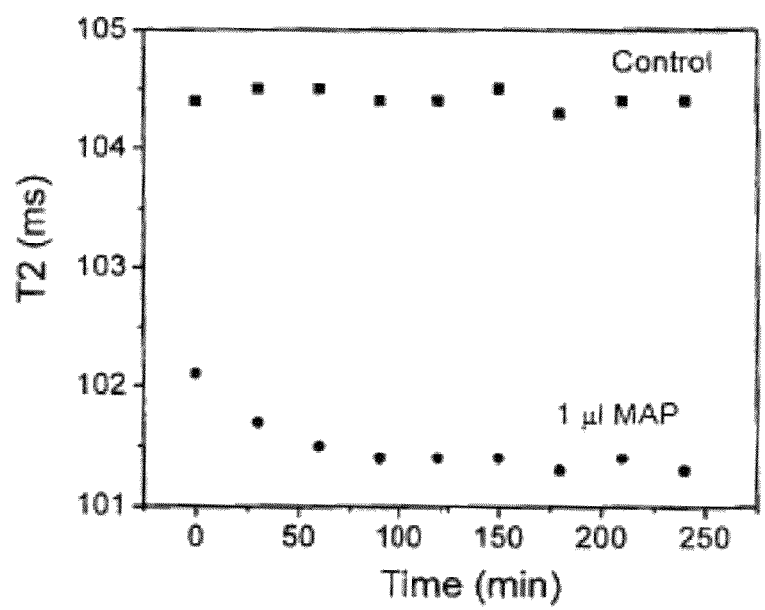
Figure 7B:
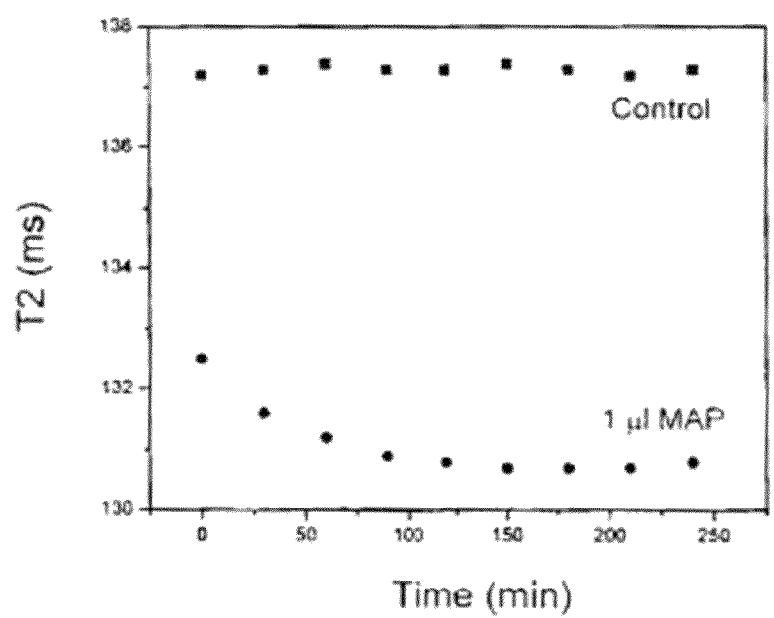

FIGS. 1, through 7(b) illustrate various aspects of the present invention. Herein, we disclose a simple water based technique for the synthesis of high quality $Fe_3O_4$ nanocrystals having high magnetic relaxivities. The method is based on the co-precipitation of ferric and ferrous chloride salts in an acidic environment, with the subsequent growth and morphology of the iron oxide crystal being controlled by addition of a polymeric capping agent at a specific time. Two different kinds of capping agents (dextran and silica) have been used in our experiments, showing that besides stabilization, the capping agents control the morphology and consequently magnetic property of the evolved particles. In our experiments, we found that rod-shaped particles of approximately 300 nm in length by about 100 nm in diameter with R2 relaxation of 300 mMs-1 were obtained when dextran was used as a capping agent. On the other hand, spherical nanoparticles of approximately 150 nm diameter with R2 relaxation of 150 mMs-1 were obtained when a coating of aminated silica was used.

The proper functionalization and bioconjugation of the nanoparticles with various targeting ligands resulted in robust nanosensors able to detect a molecular target by magnetic relaxation with high sensitivity. The high relaxivity of these particles allow us to do sensing experiments at a very low concentration of nanoparticles, with improved sensitivity and without precipitation of the particles because of their size. Furthermore, the fact that our facile synthetic method yields different sized particles depending on the polymer used is novel and can be used to generate multiple sizes and shapes of particles for further studies.

In our first set of experiments, we optimized the synthetic protocol, including the order of addition (in situ vs. step-wise), and the time of addition of the dextran polymer. Our water-based synthetic protocol involves an acid-base reaction between an acidic solution of iron salts and a basic solution of ammonium hydroxide. Upon mixing, the resulting solution becomes alkaline (pH=9.0), facilitating the formation of iron oxide nanocrystals. This initial formation of nanocrystals can occur either in the presence (in situ) or absence (step-wise) of dextran.

Since most synthetic procedures that afford stable and monodisperse nanoparticles use an in situ approach, we opted to try this approach first. In these experiments, a mixture of iron salts ($FeCl_3.6H_2O$ and $FeCl_2.4H_2O$) was dissolved in an aqueous solution of HCl. A dextran solution was prepared in aqueous ammonia solution and placed on a digital vortex mixer. Finally the resulting iron salt solution was poured at one time into the ammonia solution of dextran under vigorous stirring. Following this protocol, we obtained poorly crystalline, spherical nanocrystals of 20±5 nm in diameter and poor R2 relaxivity 15 (<1 mMs-1). This poor relaxivity contrasts with the relaxivity obtained with other published in situ procedures where relaxivity values between 60-100 mMs-1 are obtained.

We then investigated if a step-wise approach might result in larger iron oxide nanocrystals and in improved R2 relaxivity. In this approach, a dextran solution was added at a particular time after initiating the nucleation of the iron oxide crystals. In initial optimization experiments, we measured T2 relaxivity (R2) and obtained TEM images of a series of dextran iron oxide nanoparticles prepared after adding dextran at different times (1, 10, 30 and 60 sec). Following this approach, we obtained nanorods where their size, crystallinity and R2 relaxivity improved with time of addition (Table 1). No significant difference was observed between 30 and 60 seconds. Interestingly, the yield was reduced at 60 sec, based on measurements of the concentration of iron in the solution, which were performed as described. The most optimal preparation was obtained when dextran was added 30 seconds after initiating the iron oxide nucleation, resulting in dextran iron oxide nanorods (DIONrods) with an R2 of 300 mMs-1.

TABLE 1

Effect on T2 relaxivity compared to time of addition of dextran (θ) to the reaction mixture.

| Time of addition of Dextran (θ) | R2 (mM$^{-1}$S$^{-1}$) |
|---|---|
| Before adding ammonia | <1 |
| 1 sec | 50 |
| 10 sec | 150 |
| 30 sec | 300 |
| 60 sec | 300 |

I. Synthetic Procedure
Synthesis of Aminated Dextran Coated IO Nanoparticles

A mixture of iron salts containing 0.203 g $FeCl_2.4H_2O$ and 0.488 g $FeCl_3.6H_2O$ in HCl solution (88.7 12 N HCl in 2 ml water) was added to $NH_4OH$ (830 μl in 15 ml $N_2$ purged DI water) and stirred on a digital vortex mixer for 10 sec. Then, an aqueous solution of dextran (5 g in 10 ml water) was added to the mixture and stirred for 1 hr. Finally, the entire mixture was centrifuged for 30 minutes, to pellet large particles, and the supernatant was collected, filtered and washed several times with distilled water through an Amicon cell (Millipore ultrafiltration membrane YM—30 k). This process helps to get rid of the unbound dextran molecules. The dextran coated nanoparticle (3 mg, i.e. 3 ml 10 solution containing—1 mg Fe per ml) was then crosslinked by treating with 200 pl epichlorohydrin and 5 ml 0.5 M NaOH and the mixture was stirred vigorously at room temperature for 8 hrs. Afterwards, the particles were aminated by mixing 850 W, 30% ammonia and stirred overnight at RT to get aminated dextran coated 10 particles. The free epichlorohydrin was removed by washing the solution repeatedly with distilled water using an Amicon cell.

Synthesis of Aminated Silica Coated I0 Nanoparticles:

A mixture of 0.203 g $FeCl_2.4H_2O$ and 0.488 g $FeCl_3.6H_2O$ in HCl solution (88.7 μl 12 N HCl in 2 ml water) was poured into a solution of $NH_4OH$ (830 μl in 15 ml N2 purged DI water) and stirred on a digital vortex mixer. After 10 sec of stirring 2680 μl tetraethylorthosilicate, 670 μl 3-(aminopropyl)triethoxysilane and 6180 μl 3-(trihydroxysilyl)propylmethylphosphonate were added to the iron oxide nanoparticle solution and stirred for 1 hr at 3000 rpm. Then, the solution was centrifuged to remove large particles and washed finally with distilled water through Amicon cell (Millipore ultrafiltration membrane YM—30 k).

II. Advantages of the Present Method:

1) Facile, cost effective, and green chemistry synthesis that does not require vigorous experimental conditions.

2) Synthesis does not require the use of toxic reagents and therefore they are highly biocompatible.

3) Good solubility and stability of resulting particles in water, phosphate buffer saline and citrate buffer for a long time period makes them suitable for biomedical applications.

4) The resulting IO particles can be concentrated using ultrafiltration devices without inducing agglomeration of the nanoparticles.

5) The evolved particles are highly magnetic. Therefore they can be used at a very low concentration for biological applications.

6) The aminated particles can be conjugated with proteins and other biomolecules for sensing application.

7) Stable nanoparticles suspension of size range 100-500 nm (depending on experimental conditions) can be obtained.

8) Using this protocol, we can obtain iron oxide crystals of defined size and shape by simply changing the polymer used as stabilizer/coating. For example, using dextran we favor formation of rods, while using silica we favor formation of spheres, under the same general experimental conditions.

9) Other polymers can be used, potentially obtaining other shapes and sizes of nanoparticles. In particular, biodegradable or biocompatible polymers viz. polyvinyl alcohol, polyacrylic acid. among others can be used in the present method.

10) Resulting nanoparticles can be used for both in vitro and in vivo applications since synthetic procedure involves non-toxic materials.

11) Both the silica coating and dextran coating nanoparticles can achieve a strong water relaxation effect. Larger R1 and R2 are obtained.

12) Because of the larger R2 and RI. we can achieve a detectable MRI signal at low concentration of particles.

III. Characterization

A. Transmission Electron Microscopy (TEM)

The results of examination of the evolved particles by TEM are shown in FIG. 1. Shown is the TEM image of aminated (a) dextran and (b) silica coated iron oxide nanoparticles. The TEM images show that the dextran coated nanoparticles are rod shaped whereas the silica coated nanoparticles are approximately spherical in nature. (Bar=500 nm).

Figure 2:
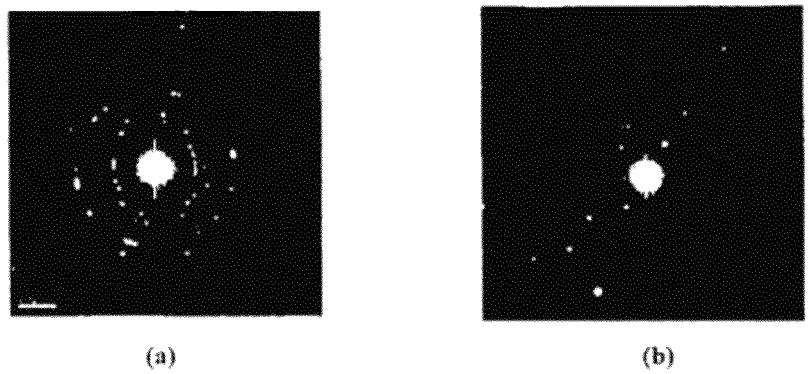
FIG. 2 is a selected area electron diffraction (SAED) image of aminated (a) dextran and (b) silica coated iron oxide nanoparticles (Bar=5 1/nm); the images show that the dextran coated particles are more crystalline than silica ones and consequently showing better magnetic relaxivity.

FIG. 2 depicts selected area electron diffraction (SAED) images of aminated (a) dextran and (b) silica coated iron oxide nanoparticles (Bar=5 1/nm). The images show that the dextran coated particles are more crystalline than silica ones and consequently showing better magnetic relaxivity.

B. X-Ray Diffraction Study (XRD)

Figure 3:
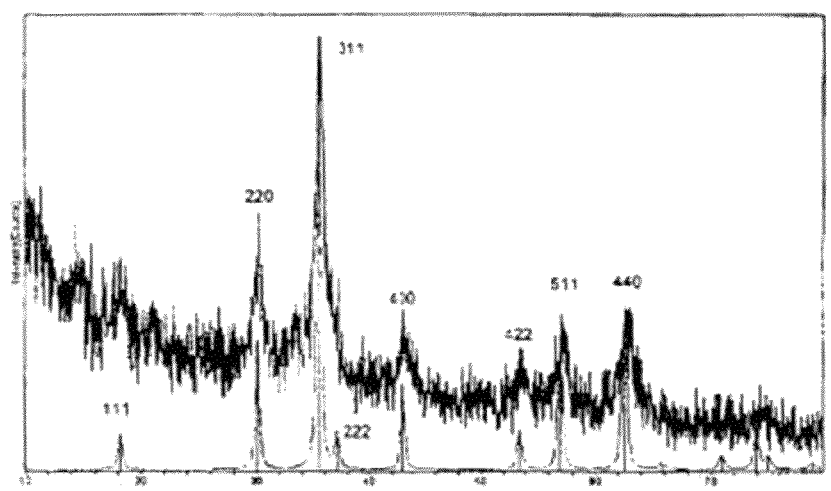
FIG. 3 shows an XRD pattern of TO nanocrystals wherein the XRD shows that the peaks matches well with that of $Fe_3O_4$ as reported in literature; both dextran and silica coated particles show same XRD pattern.

FIG. 3 shows the XRD pattern of IO nanocrystals. The XRD shows that the peaks match well with those of $Fe_3O_4$, as reported in literature. Both dextran and silica coated particles show same XRD pattern.

C. X-Ray Photoelectron Spectroscopy (XPS)

Figure 4:
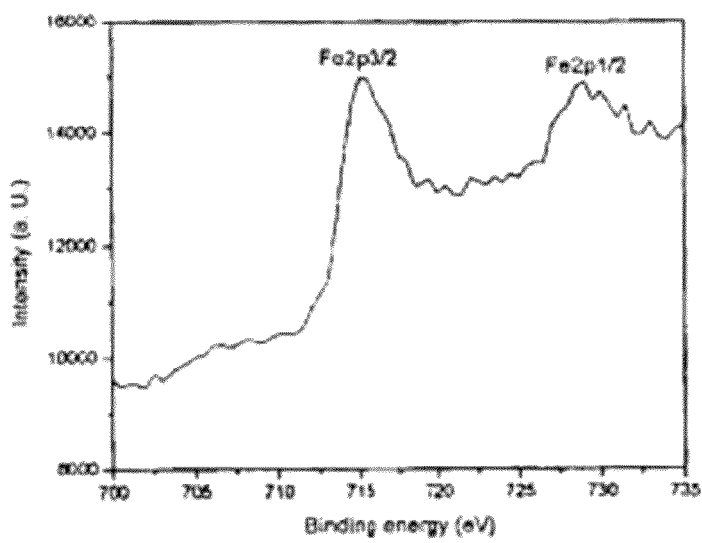
FIG. 4 provides an XPS spectrum of $Fe_3O_4$ nanocrystals where (a) shows the peaks due to Fe2p electrons and (b) shows that due to O1s electron; both dextran and silica coated particles show same XPS pattern; thus, XPS confirms the formation of $Fe_3O_4$ nanocrystals in solution.
Figure 4:
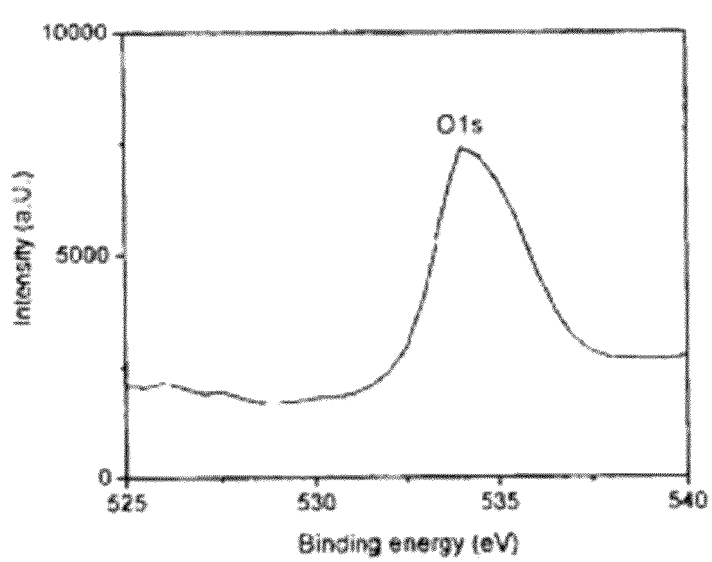

FIG. 4 provides an XPS spectrum of $Fe_3O_4$ nanocrystals where (a) shows the peaks due to Fe2p electrons and (b) shows that due to O1s electron. Both dextran and silica coated particles show same XPS pattern. XPS confirms the formation of $Fe_3O_4$ nanocrystals in solution.

D. Quantification of Amines

After amination of the resulting nanoparticles, it is important to determine the amount of amine groups present per gram of iron oxide particles. The quantification of amine group on the surface of IO particles is important, as they can be used to conjugate to a series of targets according to the amount of amines. The amine groups present per gram of iron was determined through conjugation of the aminated particles with N-succinimidyl-3-(2-pyridyldithio)propionate (SPDP). Briefly, 500 µl aminated 10 (~1 mg Fe per ml) was mixed with 100 µl 0.1 M sodium phosphate buffer (pH 7.4) and 60 µl 75 mM SPDP in DMSO and kept for 2 hrs. The unbound nanoparticles and SPDP were removed by passing the solutions through a Sephadex PD-10 column. Afterwards, a portion of the IO-SPDP conjugate was treated with 75 µl 20 mM 1,4-dithio-DL-threitol (DTT) and stirred for 2 hrs. The reaction mixture was then passed through Microcon centrifugal filter devices (YM 30) and absorbance of the filtrate was measured as previously described [Bioconjugate Chem. 1999, 10 186].

NOTE: It has been observed that the aminated IO-silica and aminated dextran particles have about 0.152 and 0.106 mmoles of amines present per gram of iron respectively. The silica coated particles are more easily aminated as the synthesis involves coating materials containing aminating agents, such as 3-(aminopropyl)triethoxysilane (APTS). On the other hand, aminated dextran coated particles are synthesized by first crosslinking the dextran coating and then aminating the crosslinked nanoparticle with ammonia. The later procedure might introduce a limited number of amino groups to the nanoparticle, as opposed to the silica/APTS protocol.

E. Characteristic Properties of Aminated Dextran and Silica Coated Iron Oxide Nanoparticles The characteristics of the aminated dextran and silica coated iron oxide particles are shown in Table 2, below.

TABLE 2

| Sample | Size (nm) | $r_1$ (mM$^{-1}$s') | r2 (m1v1$^{-1}$s$^{-1}$) | r2/r1 | mmoles of amino group per gram of iron |
|---|---|---|---|---|---|
| 10- | L - 330 | 16.80 | 296 | 17.61 | 0.106 |
| dextran-NH$_2$ | B - 100 | | | | |
| IO-silica-NH2 | ~150 | 12.43 | 145 | 11.66 | 0.152 |

F. Additional Characterization Studies

Subsequently, we studied the magnetic properties of the DIONrods. First, hysteresis loops, measured at three different temperatures (FIG. 8(a)), demonstrated a coercivitiy of 500±10 G at 5K that disappeared at 100 K and 200 K, which is typical of superparamagnetic behavior. Zero-field cooled (ZFC) and Field cooled (FC)—dc susceptibility studies (FIG. 8(b)) show that the ZFC magnetic moment increased as the temperature increased, reaching a maximum at 28 K (the blocking temperature, ($T_B$) and then it decreased with further increase in temperature. In the FC process, above the blocking temperature ($T_B$), the data followed the ZFC curve, but it deviated from ZFC curve below $T_B$ showing a slow increase in the moment with decreasing temperature. The maximum found in the ZFC curve (at $T_B$) is where a maximum number of particles exhibit superparamagnetic behavior. Below $T_B$, the relaxation times of the particles are longer than the experimental measurement time; hence the particles acquire a blocked state. In the ac susceptibility, both real and imaginary components x'(T) and x"(T), at different frequencies ranging from 1 Hz to 1 kHz exhibited a frequency dependent maximum (FIGS. 8(c) and FIG. 8(d)), which shifted to higher temperatures with increasing frequency. This may be due to either spin glass or superparamagnetic behavior. To clearly distinguish between these two behaviors, the Mydosh parameter (Φ) was calculated from the real part of the ac susceptibility according to the equation:

$$\Phi = \frac{\Delta T_m}{T_m[\Delta \log_{10}(\nu)]}$$

We used the χ'(1 Hz) and χ'(1 kHz) data to calculate Φ, obtaining a value of 0.072. $T_m$ is the temperature corresponding to the observed maximum in χ'(1 Hz) and $\Delta T_m$ is the expected for superparamagnetic systems is ~0.10, which further corroborates that our DIONrods are superparamagnetic. The particle relaxation time follows the Arrhenius law, given by:

$$\nu = \nu_0 \exp\left(\frac{-\Delta E}{k_B T}\right)$$

where ΔE/kB is the energy barrier and u is the experimental frequency. The data fitted well to a linear relation (inset of FIG. 8(d)) yielding $\Delta E/k_B$~800±10K and $T_0$~2×10$^{-14}$s, whereas 10$^{-11}$<$T_0$<10$^{-9}$s is expected for superparamagnetic systems. The lower value of $T_0$ is an indication of interparticle interactions present in the sample. Taken together, these results show that out DIONrods exhibit superparamagnetic behavior.

Figure 8:
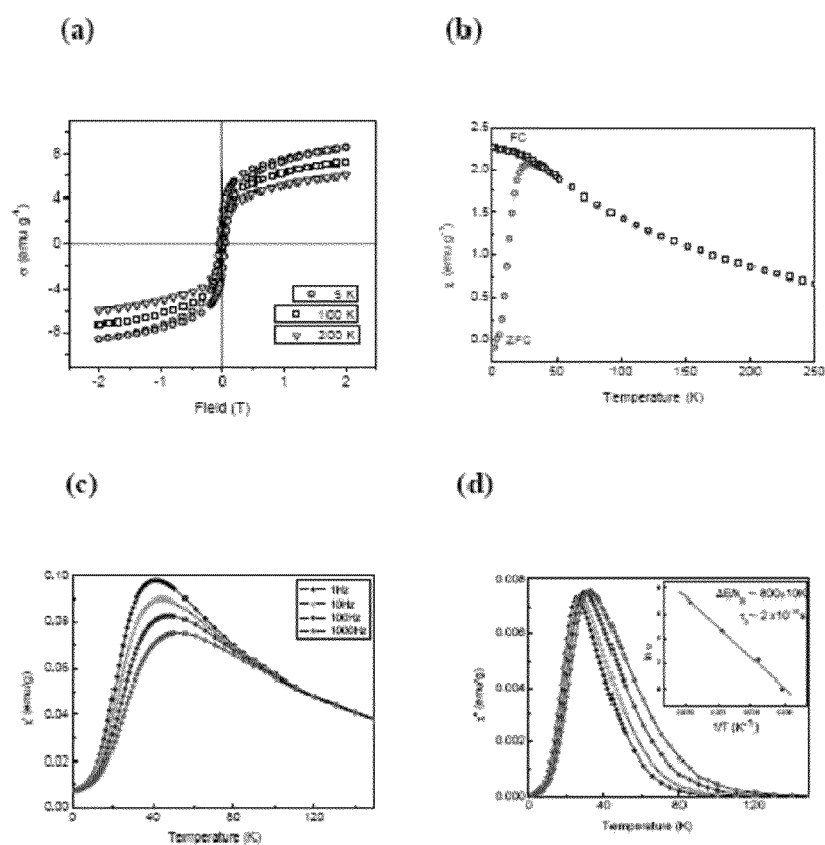
FIG. 8(a) hysteresis loops obtained at temperatures 5K, 100 K and 200 K; (b) zero field cooled and field cooled magnetic susceptibilities in an external magnetic field H=200 G; (c) real and (d) imaginary components of ac susceptibility at different frequencies, the inset of (d) shows the Arrhenius plot obtained from the imaginary component of susceptibility measurements.

Regarding FIG. 8, panel (a) shows hysteresis loops obtained at temperatures 5K, 100K and 200K, panel (b) depicts zero field cooled and field cooled magnetic susceptibilities in an external magnetic field H=200 G, panel (c) shows real and (d) imaginary components of ac susceptibility at different frequencies. The inset of FIG. (d) shows the Arrhenius plot obtained from the imaginary component of susceptibility measurements.

Furthermore, we performed experiments to assess the quality and stability of our nanorods. First, the presence of dextran on nanorod surfaces was confirmed by performing clustering experiments with Concanavalin-A (ConA). Specifically, the presence of dextran on nanoparticles can be identified via ConA-induced nanoparticle clustering, due to the strong affinity and multivalency of ConA towards carbohydrates, such as dextran. DLS experiments (FIG. 9(a)) show a time-dependent increase in particle size distribution upon ConA administration, due to formation of nanoparticle assemblies. Most importantly, a fast and reproducible change in T2 relaxation time was observed (FIG. 9(b)), not only indicating the association of dextran with the nanoparticle, but indicating the feasibility of our DIONrods as magnetic relaxation sensors.

Figure 9:
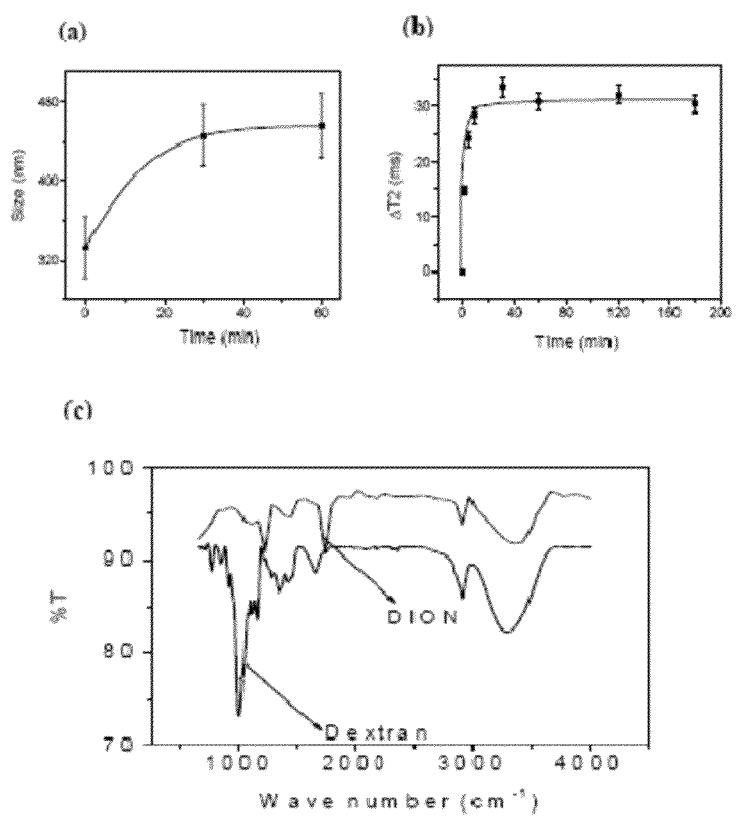
FIG. 9(a) dynamic light scattering study of DIONrods with ConA; (b) time dependent response in T2 of DIONrods (200 µl, 0.002 mg Fe per ml) when treated with 10 µl ConA (1 mg in 1 ml PBS); (c) FTIR spectra of free dextran and DIONrods.

With reference to FIG. 9(a), shown is a dynamic light scattering study of DIONrods with ConA; FIG. 9(b) shows the time dependent response in T2 of DIONrods (200 µl, 0.002 mg Fe per ml) when treated with 10 µl ConA (1 mg in 1 ml PBS); FIG. 9(c) shows FTIR spectra of free dextran and DIONrods. The FT-IR experiments further confirmed the presence of characteristic dextran peaks on the DIONrods preparations. Most importantly, the prepared DIONrods can be concentrated in PBS by ultrafiltration, obtaining highly concentrated preparations without nanoparticle precipitation even upon storage at 4° C. for over twelve months. Taken together, these results demonstrate the robustness of the dextran coating on the nanorods, making them suitable for biomedical applications.

IV. Applications

A. Conjugation with Biotin:

To conjugate biotin onto the aminated IO nanoparticles, the nanoparticle solution (1 ml) was incubated with Sulfo-N-hydroxysuccinimide-LC-Biotin (Pierce, 1 mg) for 2 hrs. The solution was then centrifuged at 13.2 k rpm for 30 min and the supernatant was discarded. The pellet was then redispersed in phosphate buffer (pH 7.4) to obtain biotinylated nanoparticles. The centrifugation and redispersion were repeated three times to get rid of unbound biotin molecules. The presence of biotin on the surface of nanoparticles was assessed via biotin-avidin interaction through magnetic relaxation. The biotin-avidin interaction is used as a model system to prove the utility of our nanoparticles as magnetic relaxation switches. The binding of avidin to the biotin of the nanoparticles causes clustering of the nanoparticles with a concomitant decrease in T2 relaxation time. The biotinylated particles were targeted with avidin and the changes in T2 was measured in a relaxometer at 0.47 T. It has been observed that even a very low concentration of the biotinylated particles can sense avidin through magnetic relaxometer.

Figure 5A:
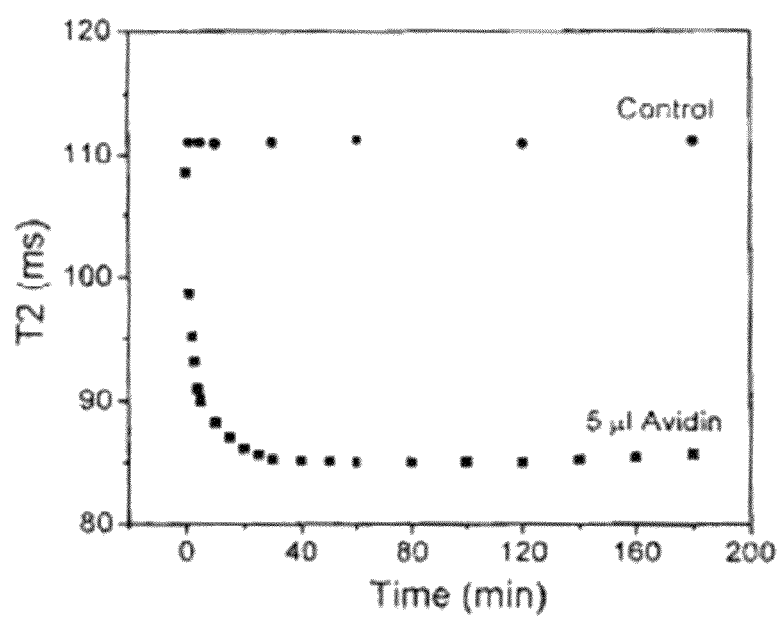
FIG. 5(a) shows a time dependent study, where after addition of 5 µg avidin in 0.5 µg IO-dextran biotin conjugate; the control contains 5 µg 0.1 M phosphate buffer, pH 7.4; 5(b) shows a time dependent study after addition of 5 µg avidin in 0.7 µg IO-silica biotin conjugate; the control contains 5 µg 0.1 M phosphate buffer at pH 7.4; 5(c) is a plot of T2 (ms) vs. Time (min) after addition of 5 µg avidin in 0.5 µg of both silica and dextran coated biotinylated IO particles; 5(d) depicts a dose dependent study where T2 was measured after 1 hr incubation of the 0.5 µg IO-dextran-biotinylated particles with avidin at different concentrations; detection limit of avidin=0.091 µg; 5(e) shows a dose dependent study where T2 was measured after 1 hr incubation of the 0.5 µg IO-silica-biotinylated particles with avidin at different concentrations; detection limit of avidin=0.071 µg.
Figure 5B:
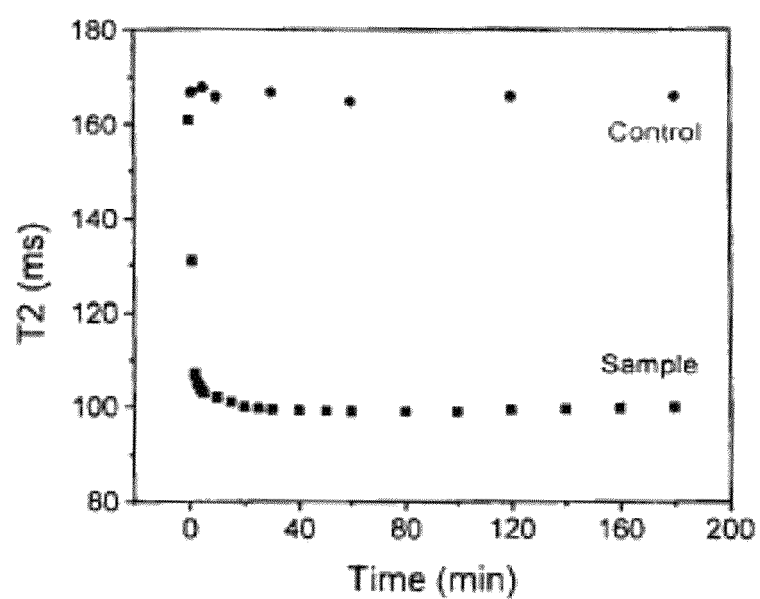
Figure 5C:
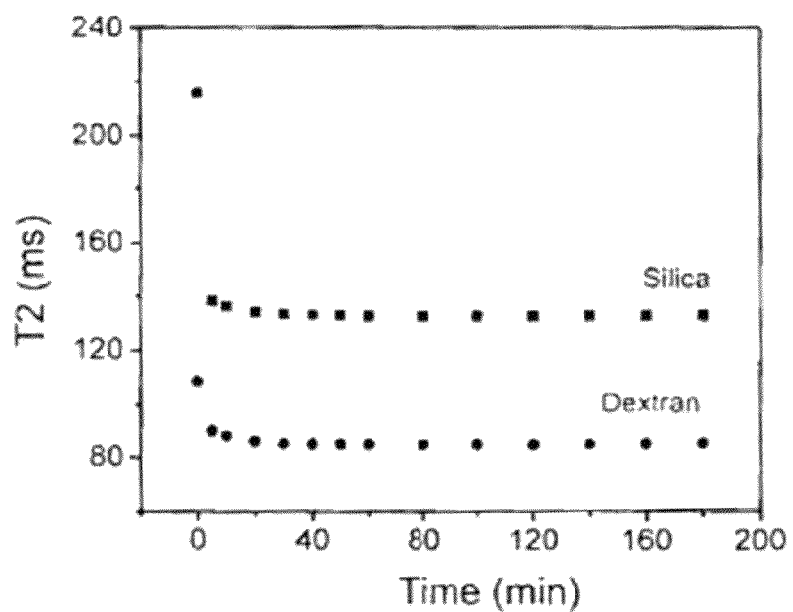

In that regard, FIG. 5(a) shows a time dependent study. After addition of 5 µg avidin in 0.5 µg IO-dextran biotin conjugate. The control contains 5 µl 0.1 M phosphate buffer at pH 7.4. FIG. 5(b) shows another time dependent study, this after addition of 5 µg avidin in 0.7 µg IO-silica-biotin conjugate. The control contains 5 µl 0.1 M phosphate buffer, pH 7.4. FIG. 5(c) shows a plot of T2 (ms) vs. Time (min) after addition of 5 µg avidin in 0.5 µg of both silica and dextran coated biotinylated IO particles. NOTE: At this concentration of iron, aminated silica coated particles show greater sensitivity than the dextran coated ones, as silica coated particles have more amine groups on their surface. Therefore. they are more biotinylated and can conjugate with avidin to a greater extent.

Figure 5D:
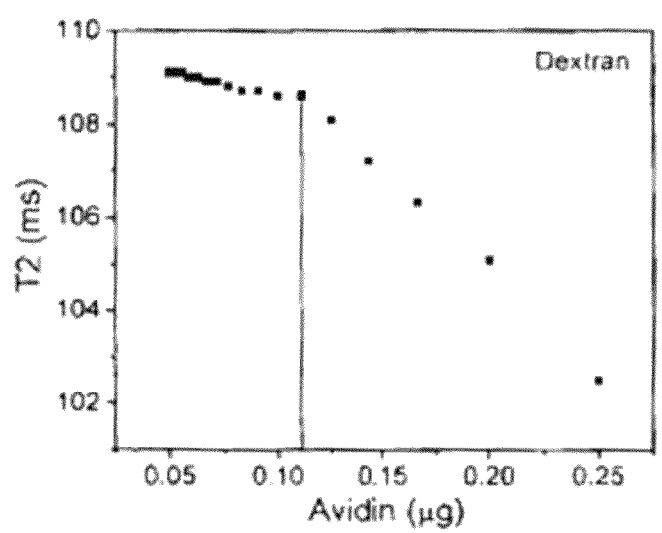

FIG. 5(d) presents a dose dependent study where T2 was measured after 1 hr incubation of the 0.5 µg IO-dextran-biotinylated particles with avidin at different concentrations. The detection limit of avidin=0.091 µg.

Figure 5E:
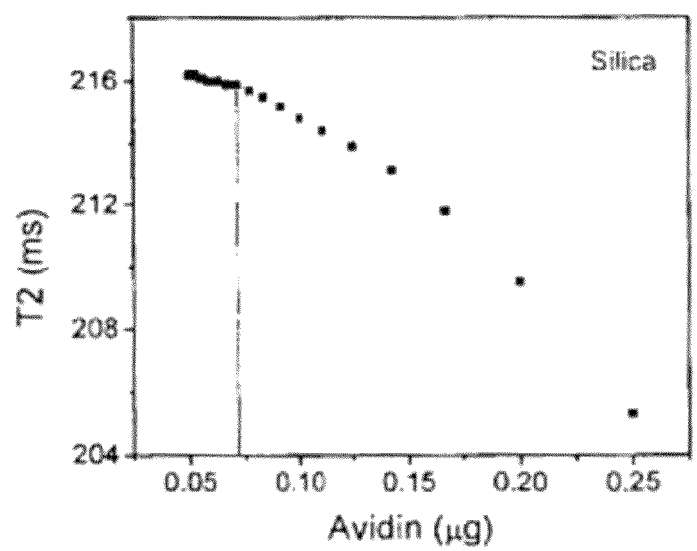

FIG. 5(e) shows another dose dependent study where T2 was measured after 1 hr incubation of the 0.5 µg IO-silica-biotinylated particles with avidin at different concentrations. Detection limit of avidin=0.071 µg. NOTE: Here also, the silica coated biotinylated 10 particles show better sensitivity with respect to dextran coated ones for avidin and can detect the presence of avidin to a lower concentration.

B. Conjugation of Protein G with Aminated Nanoparticles

To conjugate IO nanoparticles with protein G at first the particles are to be dissolved in DMSO to conjugate with disuccinimidyl suberate (DSS). The DMSO suspension of the IO nanoparticles was obtained by combining 1 ml of aminated nanoparticles with 1 ml isopropanol, mixing well and spinning down at 13.2 k rpm for 1 hr. The supernatant was decanted and the pellet was dissolved completely in 500 µl DMSO. The suspension was again treated with isopropanol and spinned down. The centrifugation and redispersion were repeated three times to get rid of trace amounts of water. Afterwards the nanoparticle pellets were again redispersed in 500 µl DMSO and to that suspension 5 µl of disuccinimidyl suberate (DSS, 5.88 mg in 128 µl DMSO) was added. The mixture was stirred well and allowed to react for 30 mins to link DSS on the surface of the particles. Then the DSS linked particles were treated with 1.5 ml isopropanol and mixed properly. The reaction mixture was centrifuged and pellets were again dispersed in DMSO. The centrifugation and redispersion was repeated for 3 times to eliminate excess DSS. Finally, the pellets were redispersed in protein G (Sigma) solution (1 mg protein G in 1 ml, 200 mM phosphate buffer, pH 8.0). The mixture was kept for 1 hr at room temperature and then overnight at 4° C. to obtain the protein G functionalized particles.

Figure 6A:
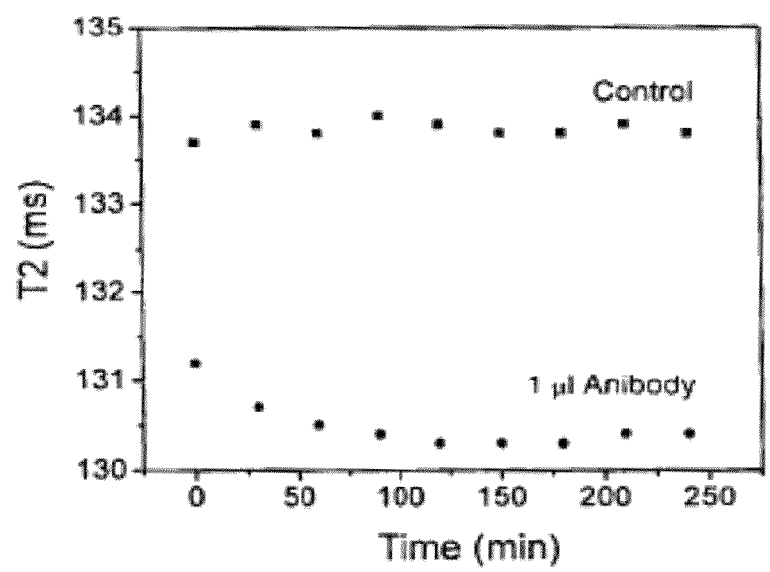
FIG. 6(a) is a time dependent study after addition of 1 µg of Antibody against Protein G in 0.42 µg IO-dextran-protein G particles; 6(b) depicts another time dependent study where after addition of 1 µg of Antibody against Protein G in 0.66 µg IO-silica-protein G particles; 7(a) is a time dependent study; after addition of 51.25 CFU MAP in 0.54 µg IO-dextran-protein G particles; control=1 µl phosphate buffer, pH 7.4; and 7(b) is a time dependent study; after addition of 51.25 CFU MAP in 0.82 µg IO-silica-protein G particles; control=1 µl phosphate buffer, pH 7.4. IO-silica-protein G was conjugated with antibody specific to MAP and then MAP was added.
Figure 6B:
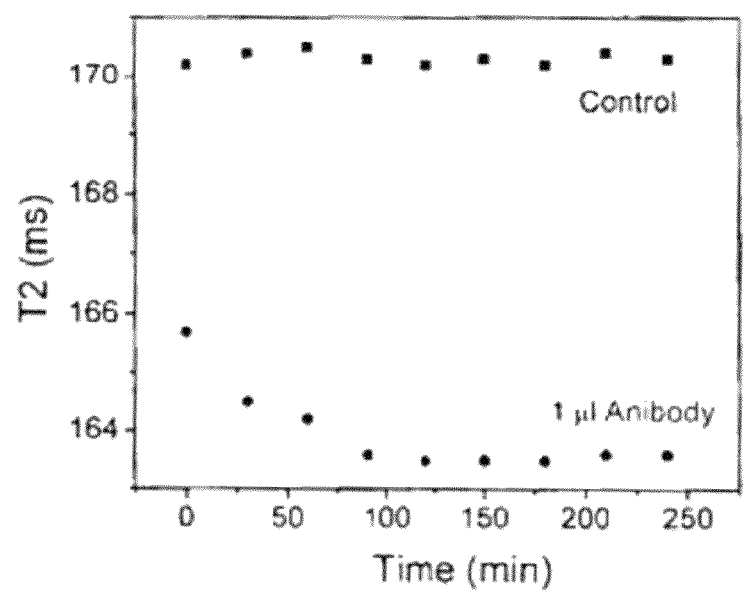

The synthesized protein G functionalized nanoparticles were targeted with an antibody against protein G and the changes in T2 were measured (FIGS. 6a and 6b). FIG. 6(a) shows a time dependent study: after addition of 1 µl of antibody against protein G in 0.42 ug IO-dextran-protein G particles. FIG. 6(b) is a time dependent study, where after addition of 1 µl of antibody against protein G in 0.66 µg IO-silica-protein G particles. NOTE: When an antibody specific to protein G was added to protein G functionalized nanoparticles, a concomitant decrease was observed due to clustering of the particles. The antibody binds to the proteins and causes clustering with other antibody conjugated particles. Consequently an instantaneous decrease in T2 was observed. The silica coated protein G functionalized particles show a greater decrease as compared to dextran coated ones. The presence of more amines on their surface of silica coated particles made them more easily bounded to protein G and causes a greater change in T2 relaxation time when treated with antibody.

C. Detection of *Mycobacterium avium paratuberculosis* (MAP)

To test the capability of our particles in sensing a "real" target we planned to use the newly synthesized protein G conjugated particles to sense the presence of bacteria in fluid media. As a model system, we used *Mycobacterium avium paratuberculosis* (MAP). A MAP specific magnetic nanosensor was prepared by conjugating an anti-MAP antibody to protein G-IO nanoparticles.

Upon addition of the bacteria to a solution containing the bacteria-specific nanosensors, a rapid and sensitive detection of the bacterial target was achieved via changes in T2. This observation proves that our relatively large iron oxide nanoparticles can be used to detect a molecular target in solution, similar to previously reported studies that use smaller nanoparticles in the range of 30-50 nm [Perez, J. M., Nat Biotechnol. 2002, 20(8): p. 816-20].

FIG. 7(a) presents the results of yet another time dependent study, after addition of 51.25 CFU MAP in 0.54 µg IO-dextran-protein G particles. The control=1 p.1 phosphate buffer, pH 7.4. IO-dextran-Protein G was conjugated with an antibody specific to MAP and then MAP was added. FIG. 7(b) is a time dependent study, showing after addition of 51.25 CFU MAP in 0.82 µg IO-silica-protein G particles. The control=1 µl phosphate buffer, pH 7.4. IO-silica-protein G was conjugated with antibody specific to MAP and then MAP was added.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A composition comprising rod-shaped iron oxide nanoparticles coated with a crosslinked aminated biocompatible polymer, the nanoparticles having R2 relaxation of approximately 300 to approximately 400 mMs$^{-1}$.

2. The composition of claim 1, wherein a lengthwise dimension of the rod-shaped nanoparticles is approximately 100 nm to approximately 500 nm.

3. The composition of claim 1, wherein said biocompatible polymer comprises dextran.

4. The composition of claim 3, wherein the rod-shaped nanoparticles further comprise a ligand conjugated to the crosslinked aminated dextran.

5. The composition of claim 3, wherein the rod-shaped nanoparticles further comprise a protein G ligand conjugated to the crosslinked aminated dextran.

6. An aqueous method of making polymer coated superparamagnetic nanoparticles, the method comprising:
   (a) providing a mixture of iron salts in aqueous hydrochloric acid;
   (b) combining a solution of ammonium hydroxide with the mixture of (a) and stirring for a time sufficient for formation of a suspension of iron oxide nanoparticles; and
   (c) adding one or more aqueous biocompatible polymers to the suspension of (b), thereby coating the nanoparticles with polymer in the presence of unreacted reagents specified in (a) and (b);
   wherein the one or more aqueous biocompatible polymers comprise:
   (i) silicon;
   (ii) polyvinyl alcohol, polyacrylic acid, a silicon-based polymer, or a combination thereof; or
   (iii) tetraethylorthosilicate, 3-(aminopropyl) triethoxysilane, 3-(trihydroxysilyl) propylmethylphosphonate, or a combination thereof.

7. The method of claim 6, wherein the biocompatible polymer comprises silicon.

8. The method of claim 6, wherein the biocompatible polymer is selected from polyvinyl alcohol, polyacrylic acid, a silicon-based polymer, and a combination thereof.

9. The method of claim 6, wherein the biocompatible polymer is selected from tetraethylorthosilicate, 3-(aminopropyl) triethoxysilane, 3-(trihydroxysilyl) propylmethylphosphonate and a combination thereof.

10. The method of claim 6, wherein the polymer coated nanoparticles have a size range of approximately 100 to approximately 500 nm.

11. The method of claim 6, further comprising waiting for a time greater than 0 seconds but less than or equal to 60 seconds before the one or more aqueous biocompatible polymers are added to the suspension of (b).

12. Spherical nanoparticles comprising iron-oxide coated with a silicon-based aminated biocompatible polymer, said nanoparticles having a diameter of approximately 100 to approximately 500 nm, and made according to the method of claim 6.

* * * * *

UNITED STATES PATENT AND TRADEMARK OFFICE
CERTIFICATE OF CORRECTION

| | |
|---|---|
| PATENT NO. | : 8,821,837 B2 |
| APPLICATION NO. | : 13/855706 |
| DATED | : September 2, 2014 |
| INVENTOR(S) | : Jesus Manuel Perez and Sudip Nath |

It is certified that error appears in the above-identified patent and that said Letters Patent is hereby corrected as shown below:

In the Specification,

Column 1, lines 17-19, contains an error in the statement regarding Federally sponsored research. The statement, which reads "This invention was made with government support under National Institutes of Health grant number K01CA101781. The government has certain rights in the invention,"

should read --This invention was made with Government support under agency contract/grant no. K01 CA101781 awarded by the National Institutes of Health. The government has certain rights in the invention.--

Signed and Sealed this
Second Day of August, 2016

Michelle K. Lee
*Director of the United States Patent and Trademark Office*